(12) United States Patent
Sakyo et al.

(10) Patent No.: US 8,672,779 B1
(45) Date of Patent: Mar. 18, 2014

(54) SYSTEM AND METHOD FOR SWING ANALYSES

(71) Applicant: Access Co., Ltd., Tokyo (JP)

(72) Inventors: Daisuke Sakyo, Tokyo (JP); Junichi Katoh, Tokyo (JP)

(73) Assignee: Access Co., Ltd., Tokyo (JP)

( * ) Notice: Subject to any disclaimer, the term of this patent is extended or adjusted under 35 U.S.C. 154(b) by 0 days.

(21) Appl. No.: 13/789,523

(22) Filed: Mar. 7, 2013

(30) Foreign Application Priority Data

Nov. 20, 2012 (JP) .................... 2012-254672

(51) Int. Cl.
    *A63B 69/36* (2006.01)
(52) U.S. Cl.
    USPC .......................................... 473/409; 473/223
(58) Field of Classification Search
    USPC ......... 473/151, 107, 212, 219, 221, 223, 224, 473/226, 453, 409
    See application file for complete search history.

(56) References Cited

U.S. PATENT DOCUMENTS

| | | | | |
|---|---|---|---|---|
| 5,688,183 | A * | 11/1997 | Sabatino et al. | 473/212 |
| 5,907,819 | A * | 5/1999 | Johnson | 702/152 |
| 5,911,635 | A * | 6/1999 | Ogden | 473/224 |
| 2005/0261073 | A1* | 11/2005 | Farrington et al. | 473/221 |
| 2005/0288119 | A1* | 12/2005 | Wang et al. | 473/223 |
| 2006/0025229 | A1* | 2/2006 | Mahajan et al. | 473/131 |
| 2006/0166737 | A1* | 7/2006 | Bentley | 463/30 |
| 2006/0166738 | A1* | 7/2006 | Eyestone et al. | 463/36 |
| 2007/0135225 | A1* | 6/2007 | Nieminen et al. | 473/212 |
| 2010/0144455 | A1* | 6/2010 | Ahern | 473/222 |
| 2011/0224012 | A1* | 9/2011 | Hashimoto et al. | 473/223 |
| 2012/0196693 | A1* | 8/2012 | Takasugi | 473/221 |

OTHER PUBLICATIONS

King, Kevin W., "The Design and Application of Wireless Mems Inertial Measurement Units for the Measurement and Analysis of Golf Swings", A dissertation submitted in partial fulfillment of the requirements for the degree of Doctor of Philosophy (Mechanical Engineering) in the University of Michigan, 2008, 149 pages.

* cited by examiner

*Primary Examiner* — Nini Legesse
(74) *Attorney, Agent, or Firm* — Morrison & Foerster LLP

(57) ABSTRACT

A swing analyzer is disclosed. The swing analyzer may be used to analyze the swing an object such as a golf club. The swing analyzer accounts for individual differences between users and/or sensors to improve performance. The swing analyzer includes a motion sensor that is attachable to the object. The motion sensor communicates wirelessly with a terminal device. The terminal device includes a swing analysis unit for performing swing analysis based on sensor data output from the motion sensor. The swing analyzer determines a target line based on position of the motion sensor while a user is at the address posture before a swing. The target line is used as a reference to provide swing analysis.

27 Claims, 8 Drawing Sheets

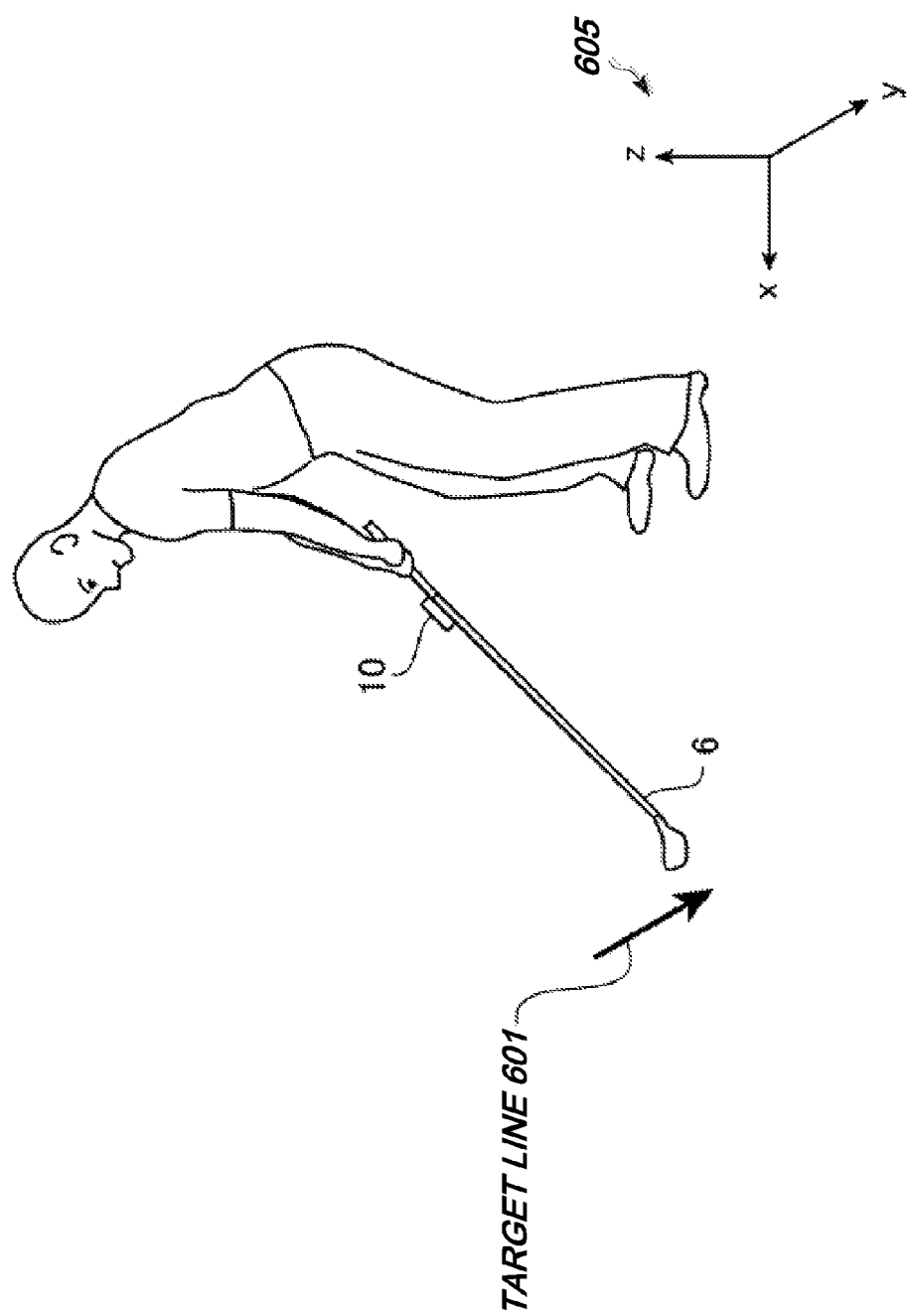

SYSTEM AND METHOD FOR SWING ANALYSES

CROSS-REFERENCE TO RELATED APPLICATION

This application claims priority to Japanese Patent Application Serial No. 2012-254672, filed Nov. 20, 2012, the contents of which are hereby incorporated by reference in their entirety for all purposes.

BACKGROUND

1. Field

The present disclosure relates to swing analyses, and more specifically relates to swing analyses using motion sensors.

2. Description of Related Art

Exemplary conventional devices for analyzing swings of objects such as sports equipment (e.g., golf clubs or baseball bats) include camera-equipped devices that capture successive images of the moving object, to which a marker is attached, until another object (e.g., a ball) is hit. Such devices are able to analyze the swing of the object based on captured images. However, such devices are limited by information that can be conveyed through images, and thus may be unable to perform certain detailed analyses. Such devices are also typically large in size, and thus may be limited in portability.

In an Internet article titled "THE DESIGN AND APPLICATION OF WIRELESS MEMS INERTIAL MEASUREMENT UNITS FOR THE MEASUREMENT AND ANALYSIS OF GOLF SWINGS," Kevin W. King describes a technique for performing swing analysis that addresses certain limitations of conventional, image-based swing analyzers. More specifically, King describes embedding a swing analysis device into the grip of a golf club that includes a compact motion sensor, a battery, and a communication module arranged in series. King further describes that, when the golf club is swung by a swing machine, data output from the compact motion sensor can be analyzed by the swing analysis device.

King's swing analyses are based on a swing machine, which provides consistent and correctly postured swings. King does not, however, consider the errors that could be introduced by human golfers or by mass-produced motion sensors.

As one example, under King's swing analysis technique, a direction that is orthogonal to a face of the golf club, at address, is used as a target line. As one of ordinary skill in the art would appreciate, a target line is an imaginary line from a golf ball to a target. The target line is useful as a reference for measuring the angle of a swing path and/or characterizing whether a swing path is inside-out, outside-in, or inside-in, among other things. The swing path of a golf club is defined as the trajectory of the head of the golf club as viewed from directly above. In King, the direction orthogonal to the face of the golf club is invariably be used as the target line because King's swing machine can take consistent address postures between swings and correct align the club face towards target each time. In contrast, it is difficult for a human golfer to have consistent postures at each swing, and/or to accurately align the face of a golf club in the direction of the target each time. King's technique does not address how an accurate target line, which is needed to accurately analyze a swing path, can be determined under these circumstances.

Moreover, King's swing analysis technique does not correct for errors that are introduced by its motion sensors. Since motion sensors are machines, they are subject to manufacturing tolerances that are caused by deviations in output. Also, motion sensors are susceptible heat buildup that can introduce output errors.

Furthermore, King's swing analysis technique assumes that a swing is made immediately after a golf club is positioned at address. In contrast, human golfers typically do not swing immediately after the address state. Rather, human golfers typically perform pre-swing movements (hereafter referred to as "waggles") before the start of a swing. The use of measurement data that is based on waggles in swing analyses can introduce errors in the corresponding results.

BRIEF SUMMARY

In one embodiment, a method of analyzing a swing of a sporting equipment using a terminal device that is configured to wirelessly receive sensor data from an equipment-mounted motion sensor comprises receiving, from the motion sensor over a wireless communication channel, a plurality of sensor data, where a sensor datum of the plurality of sensor data comprises information representing acceleration of the equipment-mounted motion sensor. The method further comprises: determining when the sporting equipment is in an address position, based on at least a portion of the received plurality of sensor data, where the address position is a starting position of the swing; determining a target line when the sporting equipment is in the address position, based on at least a portion of the received plurality of sensor data, where the target line is an imaginary line connecting the sporting equipment and a target; and characterizing a path of a swing of the sporting equipment based on the target line.

In one embodiment, a swing analysis system comprises a motion sensor configured to attach to an sporting equipment, where the motion sensor comprises an accelerometer and an angular velocity sensor; and terminal device configured to wirelessly receive accelerometer data and angular velocity data from the motion sensor. The terminal device comprises a target line setting circuitry configured to determine a position of the motion sensor when the motion sensor is in an address position, and to determine a target line based on the position; and a swing analysis circuitry configured to characterize a path of a swing of the sporting equipment based on the target line. The address position is a starting position of the swing. The target line is an imaginary line connecting the sporting equipment and a target.

In one embodiment, a non-transitory computer readable medium having computer-executable instructions, where the computer-executable instructions, when executed by one or more processors, cause the one or more processors to analyze a swing of a sporting equipment using a terminal device and an equipment-mounted motion sensor. The computer-executable instructions comprises instructions for: receiving, from the motion sensor over a wireless communication channel, a plurality of sensor data, where a sensor datum of the plurality of sensor data comprises information representing acceleration of the equipment-mounted motion sensor; determining when the sporting equipment is in an address position, based on at least a portion of the received plurality of sensor data, where the address position is a starting position of the swing;; determining a target line when the sporting equipment is in the address position, based on at least a portion of the received plurality of sensor data, where the target line is an imaginary line connecting the sporting equipment and a target; and characterizing a path of a swing of the sporting equipment based on the target line.

The motion sensor may include an accelerometer capable of detecting three-axis acceleration, where the target line setting unit obtains the position information from sensor data output from the accelerometer. Furthermore, the position information may be a vector in a gravitational acceleration direction, where the target line setting unit computes the target line in a first coordinate system, based on an outer product of the vector in the gravitational acceleration direction and a vector in a Z-axis direction.

In one embodiment, a swing analysis system comprises a motion sensor configured to attach to an sporting equipment, where the motion sensor comprises an accelerometer and an angular velocity sensor; and a terminal device configured to wirelessly receive accelerometer data and angular velocity data from the motion sensor. The terminal device comprises a swing data analysis circuitry configured to analyze a swing of the sporting equipment based on the received accelerometer data and angular velocity data; and an error correction circuitry configured to correct an output error of the motion sensor by: determining an initial position of the sporting equipment based on an initial portion of the received accelerometer data; determining an impact position of the sporting equipment based on an impact portion of the received accelerometer data; determining a difference between the initial position and the impact position; and analyzing a swing of the sporting equipment based on the difference.

The motion sensor may include an accelerometer, and the error correction unit may correct an output error of the accelerometer. The difference may be based on the time difference between the output, by the motion sensor, of the initial portion and the impact portion. The initial position may be determined by integrating the received accelerometer data over time. The impact position may be determined by integrating the received accelerometer data over time. The impact position may be determined by integrating the received accelerometer data over the time difference. The difference may be determined by equations 8-17. One or more portions of the swing analysis system may be implemented using computer circuitry and/or computer-executable instructions that are stored on a non-transitory computer-readable medium.

In one embodiment, a swing analysis system comprises: a motion sensor configured to attach to an sporting equipment, where the motion sensor comprises: an accelerometer, and an angular velocity sensor configured to detect three-axis angular velocity; and a terminal device configured to wirelessly receive accelerometer data and angular velocity data from the motion sensor, where the terminal device comprises: a swing state determination circuitry configured to determine the start of a swing based on the received accelerometer data and angular velocity data from the motion sensor; and a swing data analysis circuitry configured to analyze the swing without using at least a portion of the accelerometer data and angular velocity data from the motion sensor detected before the start of the swing.

The swing data analysis circuitry may be configured to analyze the swing without using the accelerometer data and angular velocity data from the motion sensor detected before the detected swing start point. The swing state determination circuitry may be configured to process data from the angular velocity sensor leading up to a time of swing impact and to: detect a negative peak value in Z-axis data of the angular velocity sensor within the processed data; detect a positive peak value in X-axis data of the angular velocity sensor within the processed data; determine a time representing the start of the swing, where the time representing the start of the swing is one of: a) a time at which the sign of the Z-axis data was inverted prior to the negative peak value, and b) a time at which the sign of the X-axis data was inverted prior to the positive peak value.

Furthermore, the swing state determination circuitry may be configured to identify the earlier of a) and b) as the time of the start of the swing. The accelerometer of the motion sensor may be configured to detect three-axis acceleration, and where the swing state determination circuitry may be configured to determine a time of swing impact based on Y-axis data of the accelerometer. The time of swing impact may be identified by a negative peak value of Y-axis data of the accelerometer. The time of swing impact may be identified by a rate of decrease in Y-axis data of the accelerometer over time, the rate of decrease exceeding a threshold rate. The time of swing impact may be identified by a decrease in Y-axis data of the accelerometer at a first time and at a subsequent second time exceeding a threshold value. One or more portions of the swing analysis system may be implemented using computer circuitry and/or computer-executable instructions that are stored on a non-transitory computer-readable medium.

DESCRIPTION OF THE FIGURES

FIG. 6 depicts a user coordinate system in an exemplary embodiment.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The embodiments described herein include a swing analysis system, a swing analysis method, and a swing analysis program that considers individual differences between users and/or electronic sensors to provide improved swing analyses. For the sake of simplicity, the embodiments are described with respect to sports equipment, particularly golf clubs. It should be noted, however, that the described embodiments may be adapted for use with other types of sports equipment, such as baseball bats, tennis racquets, and the like. In addition, the described embodiments may also be adapted for use with objects other than sports equipment, such as machines, the human body (e.g., arms or legs), and so forth.

Figure 1:
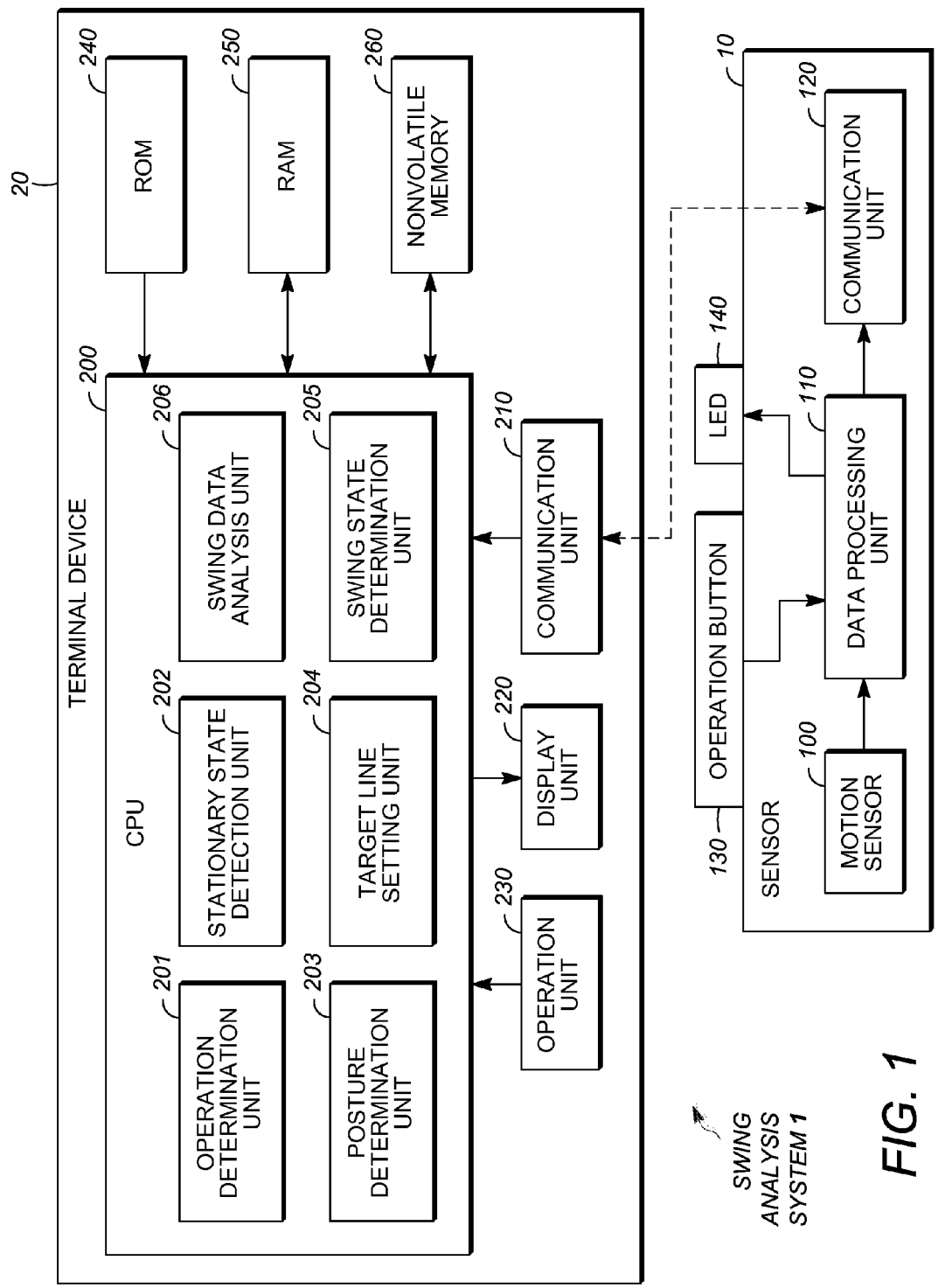
FIG. 1 is a block diagram depicting an exemplary embodiment of a swing analysis system.

FIG. 1 depicts an exemplary embodiment of a swing analysis system. As shown, exemplary swing analysis system 1 includes swing analysis sensor 10 and terminal device 20. Sensor 10 and terminal device 20 are capable of wireless communication with each other. Sensor 10 includes motion sensor 100, data processing unit 110, communication unit 120, operation button 130, and LED 140. Motion sensor 100 includes an accelerometer for detecting three-axis acceleration and an angular velocity sensor for detecting three-axis angular velocity. Motion sensor 100 may further include a geomagnetic sensor. Data processing unit 110 is a processing unit for synchronizing each piece of data detected by motion sensor 100 and outputting the processed data to communication unit 120. Data processing unit 110 may perform processes such as bias correction and/or temperature correction on the data. Communication unit 120 performs short-range wireless communication with terminal device 20. The short-range wireless communication may be carried out using technologies such as BLUETOOTH, Wi-Fi (wireless networking), and the like.

Figure 2:
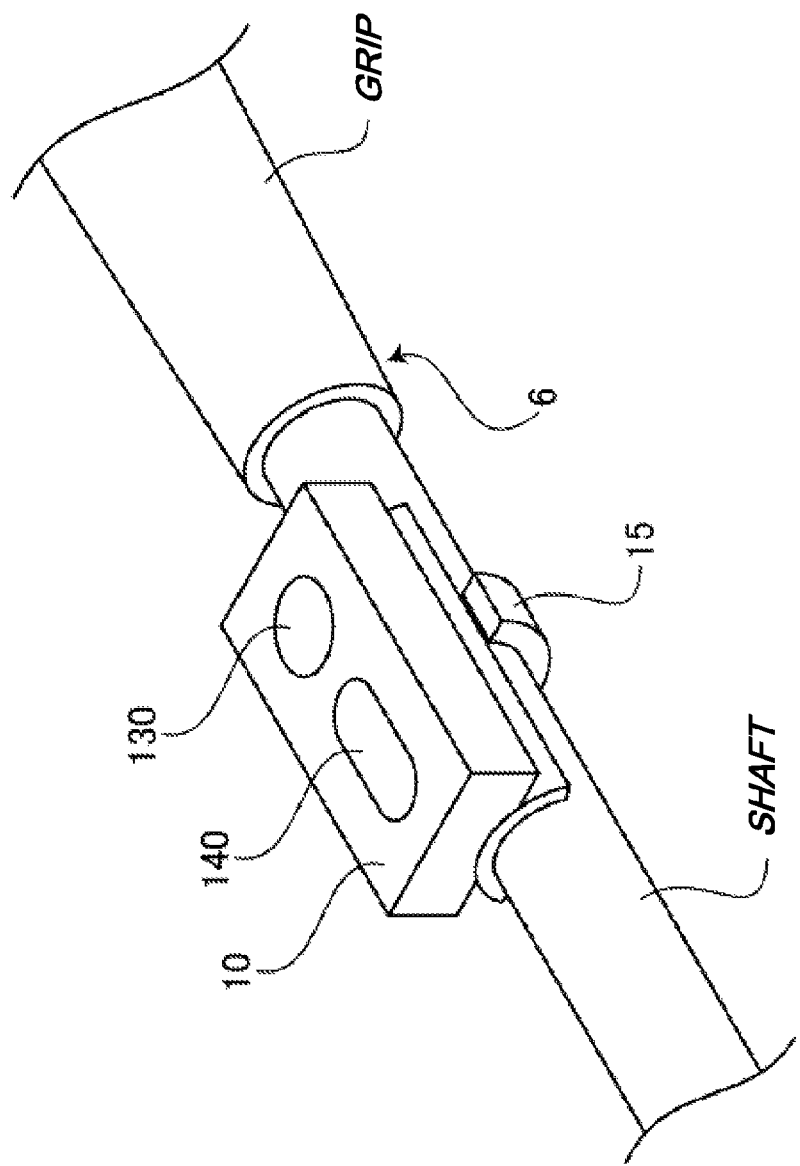
FIG. 2 is an external view depicting an exemplary embodiment of a swing analysis sensor.

FIG. 2 depicts an exemplary embodiment of swing analysis sensor 10 (FIG. 1). As shown, exemplary swing analysis sensor 10 is attached to golf club 6. Swing analysis sensor 10 is compact and has a width that is substantially equal to the shaft diameter of club golf 6. Swing analysis sensor 10 is removably attached to golf club 6 near the boundary between the grip and the shaft of golf club 6. Swing analysis sensor 10 is attached to golf club 6 with holder 15 so that it remains securely attached to golf club 6 during a golf swing, even if impact of golf club 6 with a golf ball shocks golf club 6. Holder 15 may utilize a rubber band. Sensor 10 is also lightweight so that golf club 6 does not become unbalanced when swing analysis sensor 10 is attached, and allows measurement to be taken while a user uses golf club 6 as usual. Note, in other embodiments, the adjustable size and/or tightness of holder 15 can be adapted for attachment to other sports equipment, such as baseball bats, tennis rackets, and so forth. The adjustable size and/or tightness of holder 15 can also be adapted for attachment to objects other than sports equipment, such as machines, human limbs, and so forth.

By pressing operation button 130 before swing motion, a user can start data transmission and reception between swing analysis sensor 10 and a receiving terminal device (e.g., terminal device 20 of FIG. 1) before swinging golf club 6. LED 140 may illuminate to indicate that swing analysis sensor 10 and the receiving terminal device are ready for swing analysis. LED 140 may also illuminate to indicate that a communication error between swing analysis sensor 10 and the receiving terminal device prevents swing measurement. Hence, a user can determine whether to swing by checking the illumination state of LED 140. Notably, a user need not view an error screen or other operating instruction on display unit 220 (FIG. 1) of terminal device 20 (FIG. 1) in order to discern whether the swing analysis system is ready to analyze a swing.

Referring back to FIG. 1, terminal device 20 includes central processing unit ("CPU") 200, communication unit 210, display unit 220, operation unit 230, read-only memory ("ROM") 240, random access memory ("RAM") 250, and non-volatile memory 260. During use, terminal device 20 may be placed proximate to swing analysis sensor 10 to facilitate communication. For example, terminal device 20 may be placed on a shelf in a (golf) driving range. In one embodiment, terminal device 20 is a smart phone. In other embodiments, terminal device 20 is another type of computer terminal, such as a mobile phone terminal, a personal digital assistant ("PDA"), a personal handy phone system ("PHS"), a mobile game machine, a digital home appliance, a car navigation system, a desktop PC, a laptop PC, or the like.

CPU 200 communicates with the various components of terminal device 20 to control terminal device 20. ROM 240 and non-volatile memory 260 are memories for storing various computer application programs that are executed by terminal device 20 and for storing data related to those computer application programs. RAM 250 is a volatile memory for temporarily storing data, including run-time data related to running computer application programs. RAM 250 also serves as a volatile memory into which computer application programs from ROM 240 or non-volatile memory 260 are loaded. Computer application programs stored in ROM 240 and/or non-volatile memory 260 may be executed by CPU 200.

CPU 200 performs as an operation determination unit 201, stationary state detection unit 202, posture determination unit 203, target line setting unit 204, swing state determination unit 205, and swing data analysis unit 206. In some embodiments, these units are realized by CPU 200 executing computer application programs stored in the non-volatile memory 260. In some embodiments, these units are wholly or partly implemented using application specific integrated circuitry ("ASIC") within terminal device 20. As used herein, the term "circuitry" may refer to a CPU that is executing applications programs and/or an ASIC, meaning that, for example, "a posture determination circuitry" encompass both the scenario in which CPU 200 is executing a corresponding computer application program to perform as a posture determination unit, as well as and the scenario in which an ASIC performs as a posture determination unit.

Communication unit 210 performs wireless communication with swing analysis sensor 10 via a wireless communication protocol such as BLUETOOTH. Also, communication unit 210 may include a network interface for establishing connection with an external network (such as the Internet), in order to perform data transmission and reception with the external network (such as call transmission and reception, email transmission and reception, Web content acquisition).

Operation unit 230 and display unit 220 may work in conjunction to provide a touch-based user interface. For instance, operation unit 230 may comprise a touch-sensitive panel that is sensitive to finger and/or stylus touches. Display unit 220 may be a liquid crystal display (LCD), an organic electroluminescent (OEL) display, or the like. Display unit 220 may scroll through displayed contents in response to a user's flick on operation unit 230. Display unit 220 may zoom displayed contents in response to a user's pinching gestures on operation unit 230. Operation unit 230 may have input devices (e.g., keys) other than or in addition to a touch-sensitive panel.

Figure 3A:
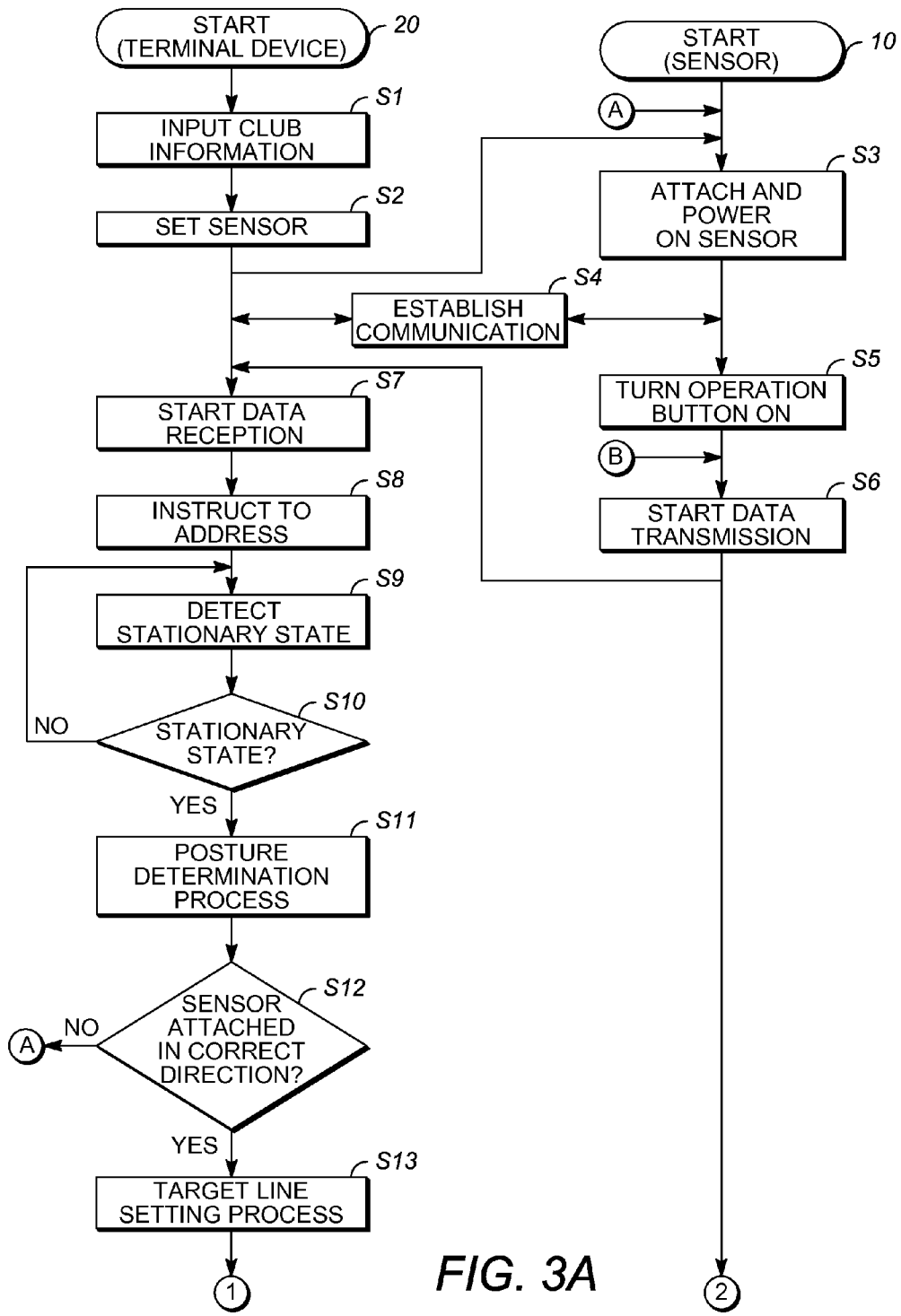
FIG. 3A is a flowchart depicting a swing analysis process in an exemplary embodiment.
Figure 3B:
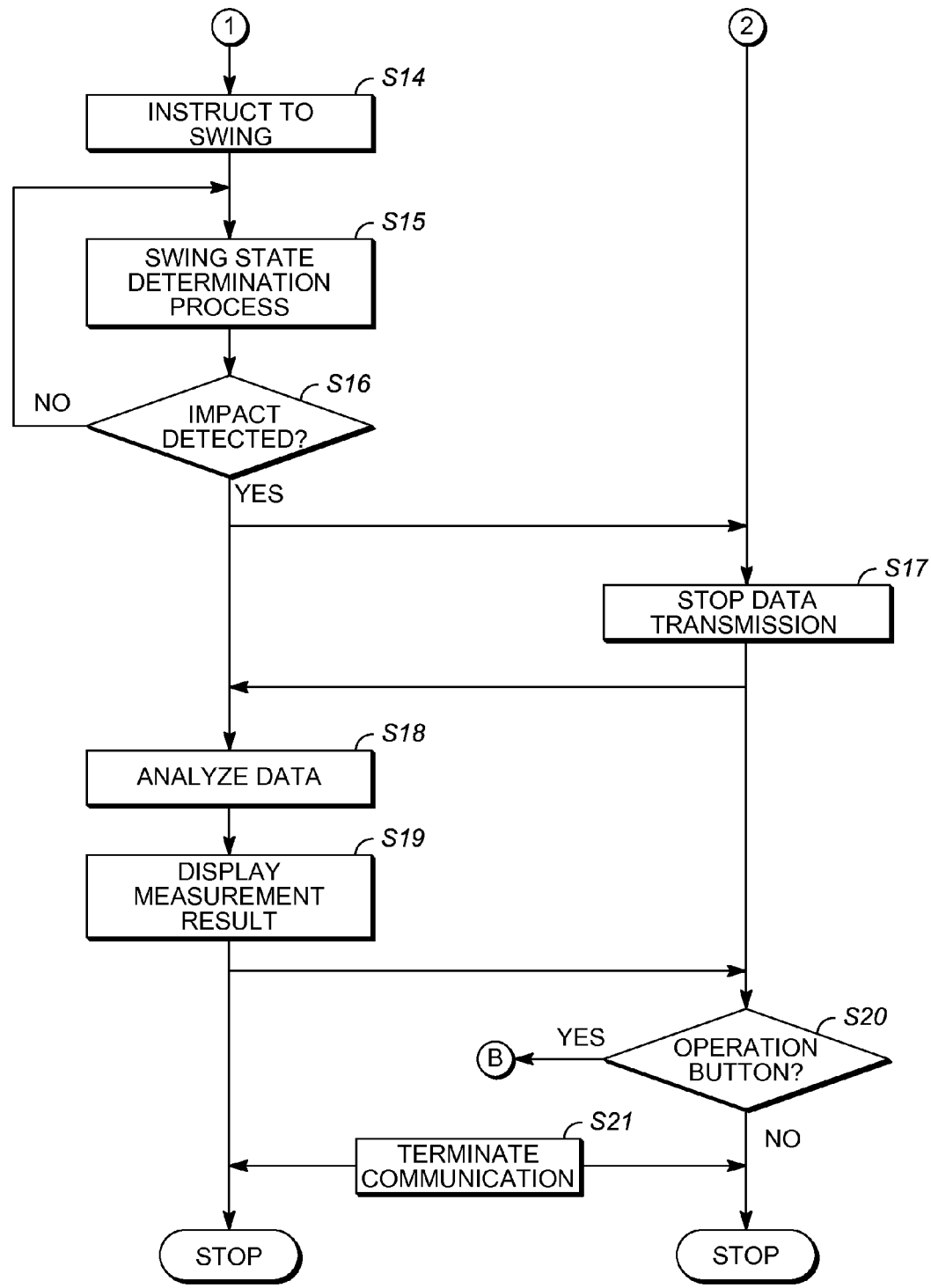
FIG. 3B is a flowchart depicting a swing analysis process in an exemplary embodiment.

An exemplary swing analysis process, used in some embodiments, is described with reference to the flowchart depicted in FIGS. 3A and 3B. Swing analysis sensor 10 and terminal device 20 of swing analysis system 1 (FIG. 1) may each carry out parts of the exemplary swing analysis process. The exemplary swing analysis process begins when a user operates the operation unit 230 (FIG. 1) in terminal device 20 (FIG. 2) to load a swing analysis application program which has been downloaded to non-volatile memory 260 (FIG. 1) of terminal device 20 (FIG. 1) beforehand. After the swing analysis application program loads, a user interface for inputting golf club information is displayed on display unit 220 (FIG. 1) of terminal device 20 (FIG. 1).

At block S1, a user inputs information regarding the golf club that is attached to swing analysis sensor 10 (FIG. 2), for example, information regarding golf club 6 (FIG. 2). Also at block S1, operation determination unit 201 (FIG. 1) of terminal device 20 (FIG. 1) acquires the golf club information and stores it in non-volatile memory 260 (FIG. 1).

At block S2, the swing analysis sensor that is to be used in the swing analysis process is selected. It is possible for more than one swing analysis sensor to be present within the wireless communication range of terminal device 20 (FIG. 1). For example, a user may have different swing analysis sensors for use with different golf clubs. This raises a need to specify, to terminal device 20 (FIG. 1), the swing analysis sensor that is to be used in an upcoming swing analysis. More specifically, at block S2, a user interface for selecting the swing analysis sensor that is to be used is displayed on display unit 220 (FIG. 1). In response to user input, operation determination unit 201 specifies the swing analysis sensor selected by the user as the current swing analysis sensor and stores the information in non-volatile memory 260 (FIG. 1). For the sake of clarity, swing analysis sensor 10 (FIG. 2) is considered to be the currently selected swing analysis sensor. Note, when a terminal device and a swing analysis sensor are first paired with each other, the swing analysis sensor may transmit its manufacturing serial number to the terminal device so that the terminal device may subsequently identify the swing analysis sensor.

At block S3, swing analysis sensor 10 (FIG. 2) is attached to a golf club (such as golf club 6 as shown in FIG. 2), and is powered on. Wireless communication is established between terminal device 20 (FIG. 1) and swing analysis sensor 10 (FIG. 2), thereby enabling data transmission and reception between the two to take place at block S4. The user then holds golf club 6 and prepares to swing. At block S5, the user presses operation button 130 (FIG. 2) of swing analysis sensor 10 (FIG. 2) to indicate readiness to swing. Note, the user may wait for a while without pressing the operation button 130 (FIG. 2) or may re-start from block S1. A user may do so in response to LED 140 (FIG. 2) indicating that the swing analysis system is not ready for swing measurement, for example.

When operation determination unit 201 (FIG. 1) of terminal device 20 (FIG. 1) detects that the operation button 130 (FIG. 2) of swing analysis sensor 10 (FIG. 2) is pressed, it instructs swing analysis sensor 10 (FIG. 2) to begin transmitting sensor data that is provided by motion sensor 100 (FIG. 1). That is, sensor data detected by the three-axis accelerometer and the three-axis angular velocity sensor of motion sensor 100 (FIG. 1) in swing analysis sensor 10 (FIG. 2) is transmitted to the terminal device 20 (FIG. 1). A certain number of pieces of data may be detected per second by the components of motion sensor 100 (FIG. 1). The data may be transmitted to terminal device 20 (FIG. 1) via data processing unit 110 (FIG. 1) and communication unit 120 (FIG. 1) as required.

At block S7, terminal device 20 (FIG. 1) receives sensor data transmitted by swing analysis sensor 10 (FIG. 2), and stores the received sensor data in RAM 250 (FIG. 1) as necessary. At block S8, terminal device 20 (FIG. 1) instructs the user to take an address posture, through the display unit 220 (FIG. 1) or a speaker (not shown). At block S9, stationary state detection unit 202 (FIG. 1) detects a stationary state based on the received sensor data. The stationary state is a state in which swing analysis sensor 10 (FIG. 2) is relatively stationary, and can be interpreted as indicating that golf club 6 (FIG. 2) is in an address position corresponding to the user's address posture. At block S9, stationary state detection unit 202 (FIG. 1) computes a mean and a standard deviation of multiple pieces of sensor data received since the start of sensor data reception in block S7. For example, 350 consecutive pieces of sensor data output by motion sensor 100 (FIG. 1) may be used in the mean and standard deviation computation. When the computed standard deviation is less than a threshold, stationary state detection unit 202 (FIG. 1) determines that the stationary state is detected. By adjusting the number of pieces of data that are used in computing a mean and standard deviation and/or the threshold based on the sensitivity of motion sensor 100 (FIG. 1), the user's age, and the golf club used, stationary state unit 202 (FIG. 1) can appropriately determine stationary states irrespective of the type of golf club that is used or the individual differences between users. When the stationary state has been detected (S10: YES), processing advances to block S11. When the stationary state has not been detected (S10: NO), processing returns to block S9 to perform stationary state detection again.

At block S11, posture determination unit 203 (FIG. 1) determines the posture of swing analysis sensor 10 using the sensor data obtained during the stationary state. More specifically, the sensor data that is obtained during the stationary state is compared with pre-existing sensor data stored in ROM 240 (FIG. 1). The pre-existing sensor data include a sign and a mean value of sensor data from each axis of the accelerometer in motion sensor 100 (FIG. 1) when swing analysis sensor 10 (FIG. 2) is attached on the golf club in a correct direction, obtained beforehand. If the sign of the sensor data at the stationary state does not match the sign of the stored sensor data or the mean of the sensor data at the stationary state differs from the mean of the stored sensor data by more than a predetermined range, then posture determination unit 203 (FIG. 1) determines that swing analysis sensor 10 (FIG. 2) is not in a correct attachment position or its position is substantially different from that associated with a normal golf address posture. By adjusting the setting of the predetermined range depending on the sensitivity of the motion sensor 100 (FIG. 1), the user's age, and the golf club used, posture determination unit 203 (FIG. 1) can determine whether correct posture is achieved during the stationary state irrespective of the type of golf club or individual differences between users. If posture determination unit 203 (FIG. 1) determines that swing analysis sensor 10 (FIG. 2) is in the correct attachment direction (S12: YES), then processing advances to block S13. If posture determination unit 203 (FIG. 1) determines that swing analysis sensor 10 (FIG. 2) is not in the correct attachment direction (S12: NO), then processing returns to S3 so that the user may re-attach swing analysis sensor 10 (FIG. 2) and repeat the subsequent process. In this way, posture determination unit 203 (FIG. 1) helps prevent a user from starting a swing when the swing analysis sensor is incorrectly attached or when the position is so substantially different from the position of a golf club in a baseline golf posture that meaningful analyses cannot be performed.

Figure 4:
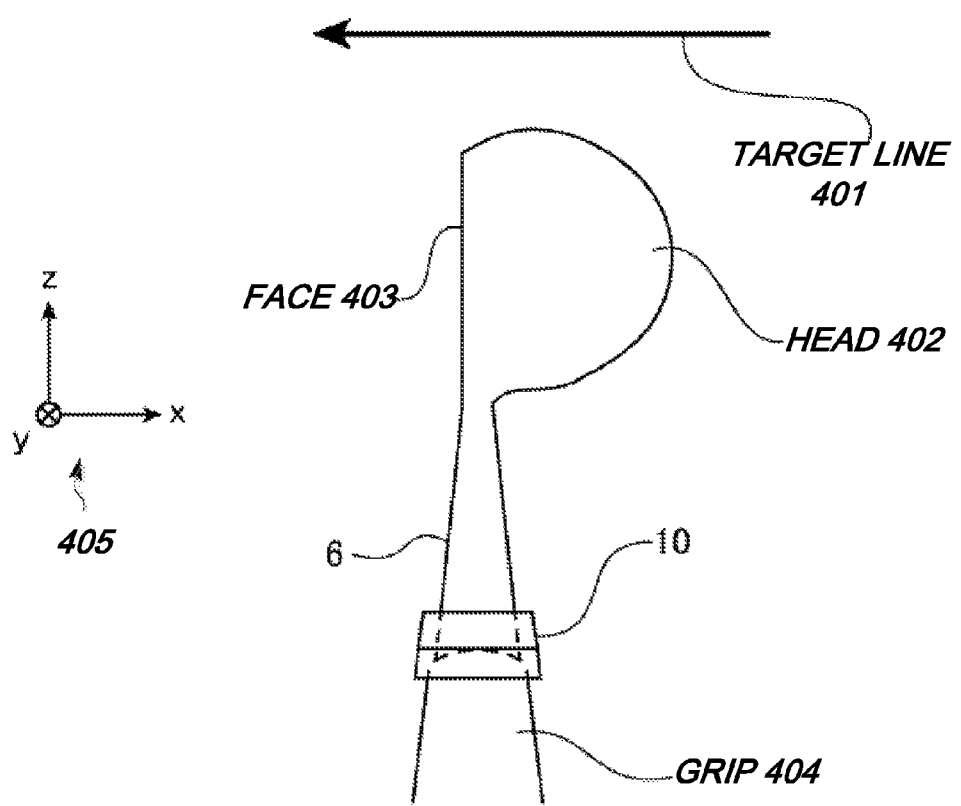
FIG. 4 depicts an exemplary golf club, swing analysis sensor, and target line in one embodiment.

It is possible that swing analysis sensor 10 (FIG. 2) cannot be attached in a position shown in FIGS. 4 and 6, depending on the location at which attachment is attempted, the diameter, material, and/or shape of the equipment to which attachment is attempted, and/or the material and/or shape of holder 15 (FIG. 2). When this occurs, swing analysis sensor 10 (FIG. 2) may be rotated, for example, by 90° clockwise, to facilitate attachment. To compensate for the rotated attachment position, the sign and/or the mean of sensor data that is obtained from motion sensor 100 (FIG. 1) of swing analysis sensor 10 (FIG. 2) can be changed. For instance, if swing analysis sensor 10 (FIG. 2) is rotated by 90° clockwise from the position shown in FIGS. 4 and 6, then the output of two of the axes measured by motion sensor 100 (FIG. 1) would be swapped. In this case, the outputs of motion sensor 100 (FIG. 1) can be rearranged prior to comparison with the pre-existing data values from ROM 240. In this way, posture determination unit 203 (FIG. 1) may function properly even when swing analysis sensor 10 is attached to a golf club differently than shown in FIGS. 4 and 6. A user may select an attachment position via operation unit 230 (FIG. 1). The selected attachment position is stored in RAM 250 (FIG. 1). The sign and the mean of the sensor data from motion sensor 100 (FIG. 1) is managed based on the attachment position stored in RAM 250 (FIG. 1).

At block S13, target line setting unit 204 (FIG. 1) determines a target line, using sensor data obtained from motion sensor 100 (FIG. 1) during the stationary state. The target line is used as a reference for determining the path of a swing (sometimes called the plane of a swing) and classifying the plane of the swing as, for example, inside-in, inside-out, or outside-in. The target line setting process is discussed in additional detail in a subsequent section.

At block S14, the user is instructed to start a swing. The instruction may be provided using display unit 220 (FIG. 1) or a speaker (not shown) of terminal device 20 (FIG. 1). Swing analysis sensor 10 (FIG. 2) measures the user's swing motion and transmits the resulting sensor data to terminal device 20 (FIG. 1). At block S15, swing state determination unit 205 (FIG. 1) of terminal device 20 (FIG. 1) performs a swing state determination process based on the received sensor data. As part of this process, individual swing states are determined and stored in RAM 250 (FIG. 1). The individual swing states may include the address state (as discussed above), swing start state (takeaway), backswing state, top of swing state, downswing state, impact state, and follow-through state. The determination of a swing start state may additionally include the error-correction of the received sensor data and/or the removing of extraneous sensor data (such as those caused by waggles). Both of processes are discussed in additional detail in subsequent sections.

At block S16, swing state determination unit 205 (FIG. 1) detects an impact of the golf club with another object (e.g., a golf ball). After impact (S16: YES), at block S17, terminal device 20 instructs swing analysis sensor 10 to stop the measurement, and the sensor 10 stops the measurement and the data transmission to terminal device 20. Note, measurement may continue for a brief moment after impact so that swing analysis sensor 10 may collect sensor data related to the follow-through state. Impact detection is discussed in additional detail in a subsequent section.

At block S18, swing data analysis unit 206 (FIG. 1) performs swing data analysis based on sensor data that is stored in RAM 250 (FIG. 1). Swing data analysis unit 206 (FIG. 1) derives, from the stored sensor data, swing measurement data. Swing measurement data may include head speed, face angle, real loft angle, lie angle, horizontal approach angle, vertical approach angle, wrist speed, wrist rotation velocity, swing plane, wrist turn coefficient, tempo, swing path coordinates, and so forth. Results from the analyses performed by swing data analysis unit 206 (FIG. 1) are stored in non-volatile memory 260 (FIG. 1). The measurements may be displayed on display unit 220 (FIG. 1) of terminal device 20 (FIG. 1). Optionally, the measurements may be transmitted from terminal device 20 (FIG. 1) to a server via a network (e.g., Internet) for storage and further management.

At block S19, the measurements are displayed on display unit 220 (FIG. 1) of terminal device 20 (FIG. 1). Display unit 220 (FIG. 1) may display swing path coordinate information using 3D graphics. The 3D graphics include a 360° view of the swing path, meaning that the display of the swing path may mimic viewpoints from various perspectives around the user. Also, information about a swing (e.g., head speed, face angle, real loft angle) at different points along the swing path can be displayed. Display elements may be used to provide measurement results in user-friendly fashions. For example, different states in a swing path may be color-coded or a seek bar may be color-coded similarly. Different display elements may also be used to differentiate the shaft of a golf club versus the swing path of the golf club.

It may be desirable to not only display (and/or record) the measurement results and the swing path, but to also present guidance information that helps a user improve his or her swing. Hence, advice may be displayed on display unit 220 (FIG. 1) based on the results of a swing analysis. More specifically, after a swing, the user uses operation unit 230 (FIG. 1) of terminal device 20 (FIG. 1) to indicate a direction that represents the actual trajectory of the golf ball. Swing data analysis unit 206 then selects an appropriate advice from pre-stored advice based on the golf ball trajectory, the head speed, the wrist speed, and/or the swing plane related to the swing, and displays the appropriate advice on display unit 220.

Typically, a user is most interested in the behavior of the golf club immediately before its impact with a golf ball. Hence, after impact is detected, sensor data from motion sensor 100 (FIG. 1) surrounding the time of impact are extracted and the corresponding calculated measurements are displayed on display unit 220 (FIG. 1). Further, the sensor data may be used to determine club face behavior (e.g., face angle displacement and path information) for display on display unit 220 (FIG. 1). Further still, the information that is displayed on display unit 220 (FIG. 1) may be presented from a bird's-eye viewpoint so that the trajectory of the swing can be readily discerned.

At block S20, swing analysis sensor 10 (FIG. 2) determines whether operation button 130 (FIG. 2) is depressed. If the operation button 130 (FIG. 2) is pressed (S20: YES), processing returns to block S6 so that swing analysis sensor 10 (FIG. 2) may be ready to analyze a new swing. If operation button 130 (FIG. 2) is not pressed (S20: NO), processing proceeds to block S21, where the communication between swing analysis sensor 10 (FIG. 2) and terminal device 20 (FIG. 1) terminates and processing ends.

1. Target Line

Recall, as discussed above, that the target line is used as a reference for measuring the angle of a swing path (e.g., whether a swing is inside-out, outside-in, or inside-in). Also recall that in King's article, the direction orthogonal to the club face can be invariably set as the target line because the swing machine can always take a constant address posture, but that King's technique fails to address the inconsistencies of human golfers. Thus, there is a possibility that correct angle measurement cannot be made because the actual target line changes depending on the address posture.

FIG. 4 illustrates club head 3 aligned with target line 1 such that the direction orthogonal to the face of club head 3 is parallel to target line 1. However, the loft angle and the lie angle of club head 3 cannot be assumed to be constant nor correct when golf club 6 is held by a human golfer. Changes (e.g., errors) in these angles affect the orthogonal direction of the golf club's face, thus making the orthogonal direction of the club face an unreliable indicator of the actual target line. Put another way, a human may not always correctly position a club face so that the club head faces the intended target. Notably, the angle of a swing path cannot be accurately measured if the measurement is based on an incorrect target line.

Figure 5A:
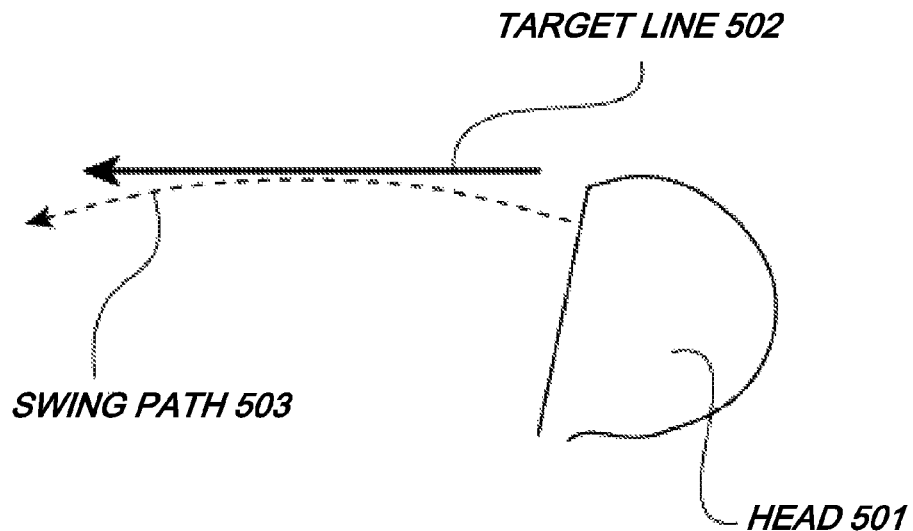
FIG. 5A depicts an exemplary swing path and target line.
Figure 5B:
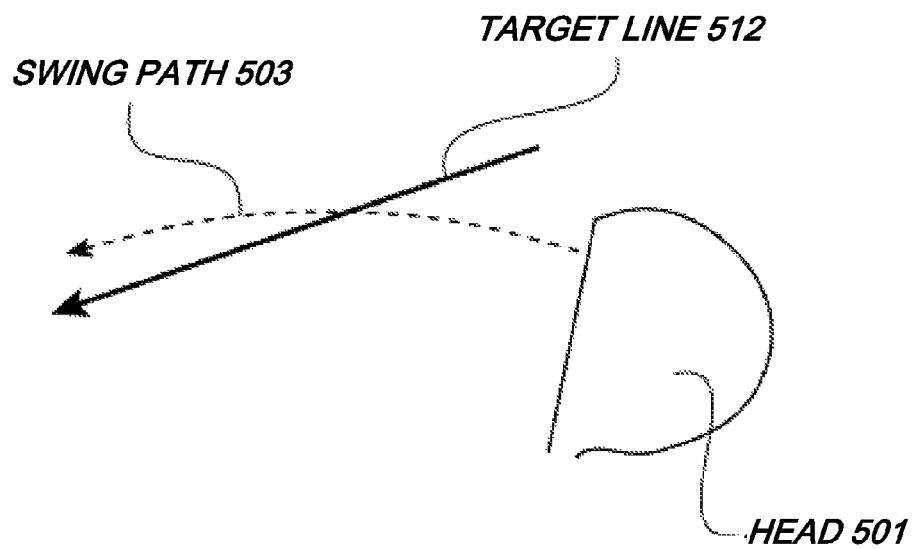
FIG. 5B depicts an exemplary swing path and target line.

FIGS. 5A and 5B each depicts the relationship between a swing path and a target line. The swing path of golf club 6 is defined by the trajectory of the head of golf club 6 as viewed from directly above. A swing path can be classified as inside-in, inside-out, or outside-in based on its relationship with the target line of the swing. In swing analysis, the inside-in swing path is typically regarded as ideal. As shown in FIG. 5A, club head 501 is swung along swing path 503. Because the entirety of swing path 503 remains inside of target path 502, swing path 503 is an inside-in swing path. In FIG. 5B, club head 501 is again swung along swing path 503. However, target line 512 as shown in FIG. 5B is skewed because of a miscalculation. Due to the miscalculation of target line 512, swing path 503 in FIG. 5B is erroneously determined as being inside-out. Thus, FIGS. 5A and 5B highlight the need to dynamically and correctly determine target lines based on the orientation of swing analysis sensor 10 (which correlates to the orientation of the shaft of golf club 6) at address, so that the swing paths can be correctly characterized.

In determining a target line, it is assumed that swing analysis sensor 10 is attached to golf club 6 such that the surface of swing analysis sensor 10 on which operation button 130 is provided is parallel to the target line, as shown in FIG. 4. More specifically, it is assumed that swing analysis sensor 10 is attached to golf club 6 such that that the X-axis in sensor coordinate system 405 is parallel to target line 401, and the Z-axis of sensor coordinate system 405 is orthogonal to target line 401. It is also assumed that, at address, the user holds golf club 6 with a stance that is parallel to the target line as shown in FIG. 6, meaning that the stance is parallel to the Y-axis in user coordinate system 605.

To determinate a target line, first, the orientation of swing analysis sensor 10 (i.e. position information of golf club 6) at address is determined using sensor data from motion sensor 100 while the swing analysis sensor is in the stationary state. Second, a target line in the sensor coordinate system is computed based on the sensor data. Third, the computed target line in the sensor coordinate system is transformed to a target line in the user coordinate system. Fourth, rotation of swing analysis sensor 10 as compared with the posture shown in FIG. 6 is computed. These processes are described in more detail, below.

When the stationary state is detected, a vector "target" of the target line in the sensor coordinate system is determined based on sensor data from the accelerometer of motion sensor 100. The vector "target" of the target line is a direction orthogonal to the gravitational acceleration direction and the Z-axis direction in sensor coordinate system 405. Accordingly, the vector "target" of the target line can be computed from an outer product of a vector in the Z-axis direction and a vector in the gravitational acceleration direction representing the position of golf club 6, as expressed by equation (1):

$$\text{target}' = Z \times g \qquad (\text{EQ. 1})$$

where "Z" represents the Z-axis of sensor coordinate system 405 and "g" represents gravitational acceleration as measured by motion sensor 100 with respect to sensor coordinate system 405.

Next, the vector "target", which is based on sensor coordinate system 405, is transformed to a vector "target" that is based on user coordinate system 605. More specifically, the vector "target" from EQ. 1 is normalized (i.e., unit-vectorized), and transformed using rotation matrices shown in EQS. (2) and (3).

$$L_{R^F} = \begin{bmatrix} \cos\gamma\sin\beta & -\sin\sigma\cos\alpha & \sin\gamma\cos\beta\sin\alpha - \sin\beta\cos\sigma\cos\alpha \\ \sin\gamma\cos\beta & \cos\sigma\cos\alpha & -\sin\beta\sin\sigma\cos\alpha - \cos\gamma\cos\beta\sin\alpha \\ \sin\beta & \sin\alpha & \cos\gamma\cos\beta\cos\sigma\cos\alpha + \sin\gamma\cos\beta\sin\sigma\cos\alpha \end{bmatrix} \qquad (\text{EQ. 2})$$

$$L_{R^F} = \begin{bmatrix} e_1^2 - e_2^2 - e_3^2 + e_4^2 & 2(e_1 e_2 - e_3 e_4) & 2(e_3 e_3 + e_2 e_4) \\ 2(e_1 e_2 + e_3 e_4) & e_2^2 - e_1^2 e_3^2 + e_4^2 & 2(e_2 e_3 - e_1 e_3) \\ 2(e_1 e_3 - e_2 e_4) & 2(e_2 e_3 + e_1 e_4) & e_3^2 - e_1^2 - e_2^2 + e_4^2 \end{bmatrix} \qquad (\text{EQ. 3})$$

The initial conditions (t=0) for $e_1$ to $e_4$ are as follows:

$$e_2(0) = \frac{\sin\alpha(0) + \cos\gamma(0)\cos\beta(0)\sin\alpha(0)}{4 e_4(0)} \qquad (\text{EQ. 4})$$

$$e_2(0) = \frac{\sin\gamma(0)\cos\beta(0)}{4 e_4(0)} \qquad (\text{EQ. 5})$$

$$e_3(0) = \frac{\sin\gamma(0)\cos\beta(0)\sin\alpha(0) - \sin\beta(0)\cos\alpha(0) - \sin\beta(0)}{4 e_4(0)} \qquad (\text{EQ. 6})$$

$$e_4(0) = \qquad (\text{EQ. 7})$$
$$\frac{1}{2}\sqrt{1 + \cos\gamma(0)\cos\beta(0) + \cos\alpha(0) + \cos\gamma(0)\cos\beta(0)\cos\alpha(0)}$$

where α(t) represents the angle between swing analysis sensor 10 (FIG. 1) and the Y-axis of sensor coordinate system 405 at time t, β(t) represents the angle between swing analysis sensor 10 (FIG. 1) and the X-axis of sensor coordinate system 405 at time t, and γ(t) represents the angle between swing analysis sensor (FIG. 1) and the Z-axis of sensor coordinate system 405 at time t.

The transformed vector "target" is not parallel to the Y-axis of user coordinate system 605. For subsequent swing analysis, the vector "target" is rotated so that it is parallel to the Y-axis of user coordinate system 605, by replacing a product of the EQ. 2 and a known rotation matrix P rotating about the Y-axis with the rotation matrix of the EQ. 2. Rotation matrix P is a rotation matrix that rotates the transformed vector "target" so that the transformed vector "target" becomes parallel to the Y-axis of user coordinate system 605. FIG. 6 illustrates transformed target 601, which is parallel to the Y-axis of user coordinate system 605.

In this way, the target line can be dynamically determined according to the orientation of swing analysis sensor 10 at address, even if golf club 6 is held at different lie and/or loft angles by different persons.

2. Accelerometer Output Correction

Recall, as discussed above, the output of motion sensor 100 may contain errors. These errors impact swing analyses. Errors may be introduced by the accelerometers used in motion sensor 100 (FIG. 2). Motion sensor 100 (FIG. 2) may employ various digital or analog accelerometers that utilize capacitive detection methods, piezoresistive detective methods, thermal detection methods, and so forth. All of these types of accelerometers are susceptible to manufacturing deviations that can introduce measurement errors. While deviations in accelerometer outputs are corrected through calibration during typical manufacturing processes, some variations persist due to low calibration precision. In addition, errors of less than 1 least significant bit (LSB) cannot be calibrated. Because the accelerometers of motion sensor 100 need to account for swing speeds upwards of 40 m/s during a golf swing, they are configured to accept a wide range of input at low sensitivity, meaning that even errors of less than 1 LSB translate to output errors that can affect swing analyses substantially. Furthermore, motion sensor 100 (FIG. 2) may heat up during operation, which also increases accelerometer errors. When accelerometer output accuracy decreases because of errors due to these issues, accurate swing measurement results cannot be obtained.

A technique for reducing overall motion sensor 100 (FIG. 2) errors by reducing accelerometer errors is discussed below. At the address posture of a golf swing, a user typically places the head of the golf club directly behind the golf ball. During the swing, the user is also expected to return to the same position so impact can be made with the golf club. It is therefore assumed that the coordinate point at swing start and the coordinate point at impact match each other. Thus, when the coordinate point at swing start, as measured by swing analysis sensor 10 (FIG. 2), is significantly different from the coordinate point at impact, as measured by swing analysis sensor 10 (FIG. 2), the position deviation is interpreted as motion sensor 100 error. To correct for such an error, sensor data from the accelerometers of motion sensor 100 are re-computed by adjusting the sensor data by the amount of acceleration that would be needed to cover the distance of the position deviation, thereby correcting any error introduced by motion sensor 100, including those that are less than 1 LSB in value and/or due to heat build-up.

The recomputation is discussed in more detail below. Note, true values are italicized in the following description and mathematical expressions. Let acceleration detected by motion sensor 100 at time t be denoted by ai(t) and true gravitational acceleration be denoted by g. Thus, true acceleration a(t) at time t is expressed by EQ. 8 and true velocity v(t) at time t is expressed by EQ. 9

$$a(t)=ai(t)-g \qquad (EQ.\ 8)$$

$$v(t)=\int a(t)dt \qquad (EQ.\ 9)$$

Further, let club head position at address be denoted by r(0), meaning that true position r(t) of the club head is expressed by EQ. 10:

$$r(t)=\int v(t)dt+r(0) \qquad (EQ.\ 10)$$

Further, let impact time be denoted by T, meaning that true impact position r(T) is expressed by EQ. 11:

$$r(T)=r(0)=r(0) \qquad (EQ.\ 11)$$

Further, let error $g_e$ represent the error that is added by motion sensor 100 to gravitational acceleration g, meaning that:

$$g=g+g_e \qquad (EQ.\ 12)$$

Acceleration a(t), the velocity v(t), and the position r(t) at time t are respectively computed according to EQS. 13 to 15:

$$a(t)=ai(t)-g=ai(t)-g-g_e=a(t)-g_e \qquad (EQ.\ 13)$$

$$v(t)=\int a(t)dt=\int a(t)dt-g_e\int 1dt=v(t)-tg_e \qquad (EQ.\ 14)$$

$$r(t)=\int v(t)dt+r(0)=\int v(t)dt-g_e\int tdt+r(0)=r(t)-(t^2/2)g_e \qquad (EQ.\ 15)$$

Moreover, error $g_e$ can be computed according to EQS. 16 and 17.

$$r(T)-r(0)=r(T)-(T^2/2)g_e-r(0)=-(T^2/2)g_e \qquad (EQ.\ 16)$$

$$g_e=-(2/T^2)(r(T)-r(0)) \qquad (EQ.\ 17)$$

where T represents the time of impact.

Thus, error $g_e$, which refers to the error that is introduced by motion sensor 100, can be computed based on measurement results that are obtained based on sensor data, and be used to correct the measurement results. As a result, the behavior of the head of golf club 6 before and after impact can be more accurately displayed.

3. Ignoring Extraneous Movements

Recall, as discussed above, a golf swing may be preceded by waggles. The analysis of waggles is not necessary to swing analysis. In fact, the inclusion of waggles into the analysis of a swing path may introduce errors because waggles are extraneous to the swing.

Some waggles are ignored by motion sensor 100 (FIG. 2) as a collateral benefit of the design of motion sensor 100. As discussed above, in order to detect the swing of a golf club having speeds upwards of 40 m/s, the configuration of the accelerometer and angular velocity sensors of motion sensor 100 are likely to favor detection range over sensitivity, meaning that each bit (including the LSB) in the output of the accelerometer and angular velocity sensors of motion sensor 100 are configured to represent relatively larger values, as compared to configurations in which the components of motion sensor 100 are set to favor sensitivity over range. Under these settings, low velocity motions, including some forms of waggles are thus automatically ignored by motion sensor 100.

Figure 7:
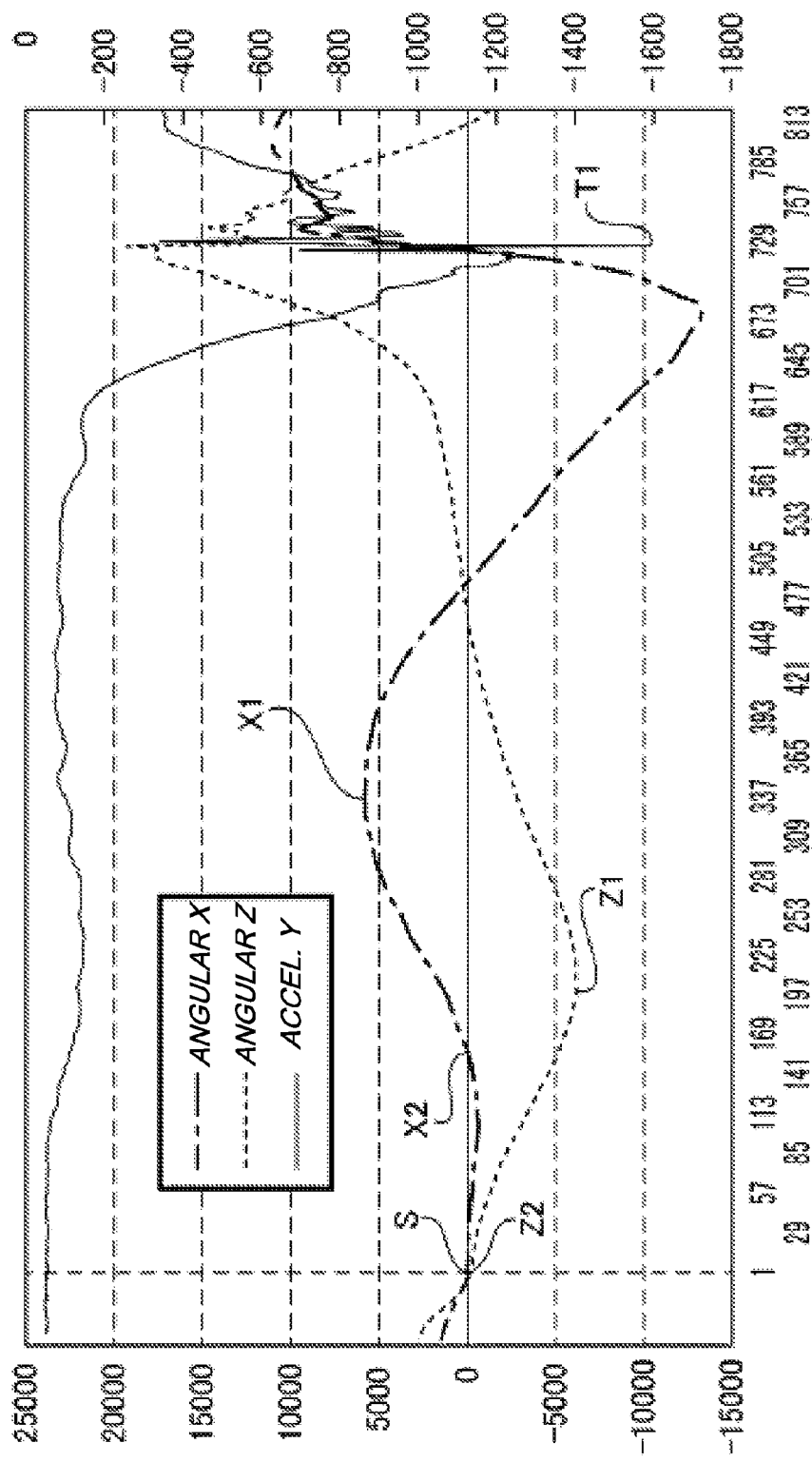
FIG. 7 depicts waveforms of swing analysis sensor data in an exemplary embodiment.

Motion sensor 100 (FIG. 2) may also employ active processes for filtering waggles. An exemplary filtering process is discussed with respect to FIG. 7. FIG. 7 depicts waveforms of the X-axis and Z-axis sensor data of the angular velocity sensor and the Y-axis sensor data of the accelerometer of the motion sensor 100 in sensor coordinate system 405, as measured during a swing of golf club 6 (FIG. 4). Swing state determination unit 205 detects negative peak value Z1 of the Z-axis sensor data of the angular velocity sensor and a positive peak value X1 of the X-axis sensor data of the angular velocity sensor from a data measurement start point, and stores those peak values in RAM 250. After detecting impact point T1, swing state determination unit 205 traces back from peak values Z1 and X1 to the respective points at which the Z-axis and the X-axis angular velocity sensor outputs were inverted in terms of sign (e.g., positive or negative). As shown in FIG. 7, swing state determination unit 205 determines point Z2 at which the Z-axis sensor data turns from the negative peak value Z1 to a positive value, and point X2 at which the X-axis sensor data turns from the positive peak value X1 to a negative value. Swing state determination unit 205 determines whether Z2 or and X2 is closer to the beginning of the swing analysis session (i.e., the start of data detection by motion sensor 100), and uses the earlier point as swing start point S. Sensor data prior to swing start point S may be filtered out.

Impact point T1 may be determined in different ways. Typically, impact with a golf ball is made at or near the downward-most position in a swing, meaning that before impact, the golf club should be accelerating downwards, and after impact, the golf club should be moving upwards. For example, the characteristic decrease in Y-axis sensor output prior to impact T1 can be seen in FIG. 7. Thus, impact point T1 may be determined by detecting a sudden decrease or a negative peak in the output of the Y-axis sensor data of the accelerometer. In addition, at impact, a golf club tends to stop (or at least slow down) momentarily to hit the ball, which produces significantly different sensor data as compared with the sensor data leading up to impact. For example, the characteristic shock in sensor output near T1 can be seen in FIG. 7. Therefore, impact point T1 may also be determined by monitoring for changes in the output waveform of the Y-axis sensor data of the accelerometer that exceed a predetermined difference. The predetermined difference may be adjusted depending on the type of golf club or golf ball that is being used, so that swing analysis sensor 10 can more accurately recognize when impact has occurred under different conditions.

Although only certain exemplary embodiments have been described in detail above, those skilled in the art will readily appreciate that many modifications are possible in the exemplary embodiments without materially departing from the novel teachings and advantages of this disclosure. For example, the above-described techniques can be adapted to analyze the swings of other types of sports equipment, such as tennis swings, baseball swings, and the like. The above-described techniques can also be used to analyze the swings of objects other than sports equipment, such as machines, the human body (e.g., limbs), and so forth. Aspects of embodiments disclosed above can be combined in other combinations to form additional embodiments. Accordingly, all such modifications are intended to be included within the scope of this technology.

What is claimed is:

1. A computer-enabled method of analyzing a swing of a sporting equipment using a terminal device that is configured to wirelessly receive sensor data from an equipment-mounted motion sensor, the method comprising:
   receiving, from the motion sensor over a wireless communication channel, a plurality of sensor data, wherein a sensor datum of the plurality of sensor data comprises information representing acceleration of the equipment-mounted motion sensor;
   determining when the sporting equipment is in an address position, based on at least a portion of the received plurality of sensor data, wherein the address position is a starting position of the swing;
   determining, from at least a portion of the received plurality of sensor data, a vector indicating a gravitational acceleration direction with respect to a first coordinate system,
      wherein the first coordinate system comprises three orthogonal axes,
      wherein the three orthogonal axes are an x-axis and a y-axis that define an x-y plane, and a z-axis,
      wherein the x-y plane is parallel to the length of the sporting equipment;
   determining a target line for the sporting equipment at the address position, by computing the outer product of the vector indicating the gravitational acceleration direction and a vector representing the z-axis,
      wherein the target line is an imaginary line connecting the address position and a target; and
   characterizing a path of a swing of the sporting equipment based on the target line.

2. The method according to claim 1, further comprising:
   determining a transformed target line by transforming the target line in the first coordinate system to a second coordinate system,
   wherein the second coordinate system comprises three orthogonal axes,
   wherein the three orthogonal axes include an x-axis and a y-axis, and
   wherein the length of the sporting equipment, at the address position, is parallel to the x-axis.

3. The method according to claim 2, wherein:
   the transformed target line is orthogonal to the x-axis and is parallel to the y-axis of the second coordinate system.

4. The method according to claim 1, further comprising:
   determining, based on at least a portion of the received plurality of sensor data, when the sporting equipment is in a stationary state, wherein the determining of the stationary state comprises:
      determining a mean and a standard deviation of the at least a portion of the received plurality of sensor data;
      comparing the standard deviation against a threshold.

5. The method according to claim 4, wherein:
   the number of sensor data in the portion and the threshold are based on at least one of a sensitivity of the motion sensor, a user's age, and the type of the sporting equipment.

6. The method according to claim 4, further comprising:
   determining whether the sporting equipment is correctly positioned during the stationary state of the motion sensor.

7. The method according to claim 6, further comprising:
   receiving a user input indicating that the sporting equipment is in a baseline position, the baseline position representing a baseline starting position for the swing;
   receiving, from the motion sensor, a baseline plurality of sensor data representing the baseline starting position;
   determining a baseline mean of the baseline plurality of sensor data, wherein the baseline mean comprises a value and a sign;
   determining, from at least a portion of the received plurality of sensor data, a current mean of the at least a portion of received plurality of sensor data, wherein the current mean comprises another value and another sign; and
   determining that the sporting equipment is correctly positioned if:
      the sign of the baseline mean and the sign of the current mean are the same, and
      the value of the baseline mean and the value of the current mean differ by less than a threshold.

8. The method according to claim 1, wherein:
   the sporting equipment is a golf club.

9. The method according to claim 8, wherein:
   the characterizing characterizes a path of a swing of the sporting equipment as an inside-in, outside-in, or inside-out golf swing.

10. A swing analysis system comprising:
a motion sensor configured to attach to a sporting equipment, wherein the motion sensor:
comprises an accelerometer and an angular velocity sensor, and
is configured to attach to the sporting equipment along a surface plane defined by an x-axis and a y-axis of a first coordinate system,
wherein the x-axis, the y-axis, and a z-axis of the first coordinate system are orthogonal, and
wherein the surface plane defined by the x-axis and the y-axis of the first coordinate system is parallel to the length of the sporting equipment at an address position; and
a terminal device configured to wirelessly receive accelerometer data and angular velocity data from the motion sensor, wherein the terminal device comprises:
a target line setting circuitry configured to:
determine a position of the motion sensor when the motion sensor is in the address position, wherein the address position is a starting position of the swing, and
determine a target line based on the position, wherein:
the target line is an imaginary line connecting the sporting equipment and a target, and
is based on an outer product of:
the vector indicating the gravitational acceleration direction with respect to the first coordinate system, and
a vector representing an z-axis direction of the first coordinate system; and
a swing analysis circuitry configured to characterize a path of a swing of the sporting equipment based on the target line.

11. The swing analysis system according to claim 10,
wherein the target line setting circuitry is configured to determine a transformed target line by transforming the target line in the first coordinate system to a second coordinate system,
wherein the second coordinate system comprises three orthogonal axes,
wherein the three orthogonal axes include an x-axis and a y-axis, and
wherein the length of the sporting equipment, at the address position, is parallel to the x-axis.

12. The swing analysis system according to claim 11, wherein:
the transformed target line is orthogonal to the x-axis and is parallel to the y-axis of the second coordinate system.

13. The swing analysis system according to claim 11, further comprising a stationary state detection circuitry configured to:
determine a mean and a standard deviation of a plurality of sensor data from the motion sensor;
determine that the motion sensor is in a stationary state when the standard deviation is less than a threshold.

14. The swing analysis system according to claim 13, wherein:
the number of sensor data in the plurality of sensor data and the threshold are based on at least one of a sensitivity of the motion sensor, a user's age, and the type of the sporting equipment.

15. The swing analysis system according to claim 14, wherein:
the accelerometer is configured to detect acceleration in three axes.

16. The swing analysis system according to claim 13, further comprising:
a posture determination circuitry configured to determine whether the motion sensor is correctly positioned during the stationary state of the motion sensor.

17. The swing analysis system according to claim 16, wherein the posture determination circuitry is configured to:
receive a user input indicating that the motion sensor is in a baseline position, the baseline posture representing that the sporting equipment is in a baseline starting position for the swing;
receive, from the motion sensor, a baseline plurality of sensor data representing the baseline starting position;
determine a baseline mean of the baseline plurality of sensor data, wherein the baseline mean comprises a value and a sign;
determine, from at least a portion of the received plurality of motion sensor, a current mean of the current plurality of sensor data, wherein the current mean comprises another value and another sign; and
determine that the motion sensor is correctly positioned if:
the sign of the baseline mean and the sign of the current mean are the same, and
the value of the baseline mean and the value of the current mean differ by less than a threshold.

18. The swing analysis system according to claim 16,
wherein the sporting equipment is a golf club and
wherein the motion sensor is sized to attach to a shaft of the golf club.

19. A non-transitory computer readable medium having computer-executable instructions, wherein the computer-executable instructions, when executed by one or more processors, cause the one or more processors to analyze a swing of a sporting equipment using a terminal device and an equipment-mounted motion sensor, the computer-executable instructions comprising instructions for:
receiving, from the motion sensor over a wireless communication channel, a plurality of sensor data, wherein a sensor datum of the plurality of sensor data comprises information representing acceleration of the equipment-mounted motion sensor;
determining when the sporting equipment is in an address position, based on at least a portion of the received plurality of sensor data, wherein the address position is a starting position of the swing;
determining, from at least a portion of the received plurality of sensor data, a vector indicating a gravitational acceleration direction with respect to a first coordinate system,
wherein the first coordinate system comprises three orthogonal axes,
wherein the three orthogonal axes are an x-axis and a y-axis that define an x-y plane, and a z-axis,
wherein the x-y plane is parallel to the length of the sporting equipment;
determining a target line for the sporting equipment at the address position, by computing the outer product of the vector indicating the gravitational acceleration direction and a vector representing the z-axis,
wherein the target line is an imaginary line connecting the sporting equipment and a target; and
characterizing a path of a swing of the sporting equipment based on the target line.

20. The non-transitory computer readable medium according to claim 19, further comprising computer-executable instructions for:

determining a transformed target line by transforming the target line in the first coordinate system to a second coordinate system, wherein the second coordinate system comprises three orthogonal axes, wherein the three orthogonal axes include an x-axis and a y-axis, and wherein the length of the sporting equipment, at the address position, is parallel to the x-axis.

21. The non-transitory computer readable medium according to claim 20, wherein:

the transformed target line is orthogonal to the x-axis and is parallel to the y-axis of the second coordinate system.

22. The non-transitory computer readable medium according to claim 19, further comprising computer-executable instructions for:

determining, based on at least a portion of the received plurality of sensor data, when the sporting equipment is in a stationary state, wherein the determining of the stationary state comprises:

determining a mean and a standard deviation of the at least a portion of the received plurality of sensor data;

comparing the standard deviation against a threshold.

23. The non-transitory computer readable medium according to claim 22, wherein: the number of sensor data in the portion and the threshold are based on at least one of a sensitivity of the motion sensor, a user's age, and the type of the sporting equipment.

24. The non-transitory computer readable medium according to claim 22, further comprising computer-executable instructions for:

determining whether the sporting equipment is correctly positioned during the stationary state of the motion sensor.

25. The non-transitory computer readable medium according to claim 24, further comprising computer-executable instructions for:

receiving a user input indicating that the sporting equipment is in a baseline position, the baseline position representing a baseline starting position for the swing;

receiving, from the motion sensor, a baseline plurality of sensor data representing the baseline direction position;

determining a baseline mean of the baseline plurality of sensor data, wherein the baseline mean comprises a value and a sign;

determining, from at least a portion of the received plurality of sensor data, a current mean of the at least a portion of received plurality of sensor data, wherein the current mean comprises another value and another sign; and determining that the sporting equipment is correctly positioned if:

the sign of the baseline mean and the sign of the current mean are the same, and the value of the baseline mean and the value of the current mean differ by less than a threshold.

26. The non-transitory computer readable medium according to claim 19, wherein:

the sporting equipment is a golf club.

27. The non-transitory computer readable medium according to claim 26, wherein:

the characterizing characterizes a path of a swing of the sporting equipment as an inside-in, outside-in, or inside-out golf swing.

* * * * *